United States Patent
Arakawa

(10) Patent No.: US 12,042,328 B2
(45) Date of Patent: Jul. 23, 2024

(54) INFORMATION PROCESSING DEVICE, WEARABLE DEVICE, INFORMATION PROCESSING METHOD, AND STORAGE MEDIUM

(71) Applicant: NEC Corporation, Tokyo (JP)

(72) Inventor: Takayuki Arakawa, Tokyo (JP)

(73) Assignee: NEC CORPORATION, Tokyo (JP)

( * ) Notice: Subject to any disclaimer, the term of this patent is extended or adjusted under 35 U.S.C. 154(b) by 535 days.

(21) Appl. No.: 17/299,005

(22) PCT Filed: Dec. 19, 2018

(86) PCT No.: PCT/JP2018/046879
§ 371 (c)(1),
(2) Date: Jun. 2, 2021

(87) PCT Pub. No.: WO2020/129197
PCT Pub. Date: Jun. 25, 2020

(65) Prior Publication Data
US 2022/0039779 A1    Feb. 10, 2022

(51) Int. Cl.
*A61B 8/08* (2006.01)
*A61B 8/02* (2006.01)
(Continued)

(52) U.S. Cl.
CPC .............. *A61B 8/02* (2013.01); *A61B 8/5223* (2013.01); *A61B 8/4209* (2013.01); *G16H 40/63* (2018.01)

(58) Field of Classification Search
CPC ............ A61B 8/02; A61B 5/02; A61B 8/5223
See application file for complete search history.

(56) References Cited

U.S. PATENT DOCUMENTS 6,730,029 B1 * 5/2004 Moriya ................ G01N 29/348
600/437
2008/0281169 A1   11/2008 Akkermans et al.
(Continued)

FOREIGN PATENT DOCUMENTS

CN     108113706 B  *  1/2021  ............... A61B 8/02
JP     2006014916 A  *  1/2006  .......... G01S 15/8954
(Continued)

OTHER PUBLICATIONS

Jeger-Madiot et al. Non-contact and through-clothing measurement of the heart rate using ultrasound vibrocardiography, Medical Engineering & Physics, vol. 50, 2017, pp. 96-102, ISSN 1350-4533, https://doi.org/10.1016/j.medengphy.2017.09.003.) (Year: 2017).*
(Continued)

*Primary Examiner* — Angela M Hoffa
*Assistant Examiner* — Younhee Choi
(74) *Attorney, Agent, or Firm* — Sughrue Mion, PLLC

(57) ABSTRACT

Provided is an information processing device including: an inspection signal generation unit configured to generate an inspection signal for emitting an inspection sound toward an ear canal of a subject; a first acoustic information acquisition unit configured to acquire a first acoustic information including information about an echo sound of the inspection sound; and a heartbeat information acquisition unit configured to acquire a heartbeat information about a heartbeat of the subject based on the first acoustic information.

10 Claims, 8 Drawing Sheets

(51) Int. Cl.
    *A61B 8/00*     (2006.01)
    *G16H 40/63*    (2018.01)

(56) References Cited

U.S. PATENT DOCUMENTS

| | | | | |
|---|---|---|---|---|
| 2009/0299215 | A1* | 12/2009 | Zhang | H04R 25/30 |
| | | | | 600/559 |
| 2012/0197093 | A1* | 8/2012 | LeBoeuf | A61B 5/7203 |
| | | | | 250/226 |
| 2013/0197377 | A1 | 8/2013 | Kishi et al. | |
| 2014/0051940 | A1 | 2/2014 | Messerschmidt | |
| 2017/0070834 | A1 | 3/2017 | Ben-Ami et al. | |
| 2019/0380677 | A1* | 12/2019 | Ono | A61B 8/4236 |

FOREIGN PATENT DOCUMENTS

| | | |
|---|---|---|
| JP | 2010-017317 A | 1/2010 |
| JP | 2012-130391 A | 7/2012 |
| JP | 2012-249884 A | 12/2012 |
| JP | 2013-153782 A | 8/2013 |
| JP | 2014-087387 A | 5/2014 |
| JP | 2016-036617 A | 3/2016 |
| JP | 2016-158878 A | 9/2016 |
| JP | 2017-528011 A | 9/2017 |

OTHER PUBLICATIONS

Fan et al. 2023. APG: Audioplethysmography for Cardiac Monitoring in Hearables. In The 29th Annual International Conference on Mobile Computing and Networking (ACM Mobi Com '23), Oct. 2-6, 2023, Madrid, Spain. ACM, New York, NY, USA, 15 pages. https://doi.org/10.1145/3570361.3613281. (Year: 2023).*

International Search Report for PCT Application No. PCT/JP2018/046879, mailed on Mar. 19, 2019.

English translation of Written opinion for PCT Application No. PCT/JP2018/046879, mailed on Mar. 19, 2019.

* cited by examiner

INFORMATION PROCESSING DEVICE, WEARABLE DEVICE, INFORMATION PROCESSING METHOD, AND STORAGE MEDIUM

TECHNICAL FIELD

The present invention relates to an information processing device, a wearable device, an information processing method, and a storage medium.

BACKGROUND ART

Patent Literature 1 discloses a pulse measuring device that calculates a pulse rate by detecting an arterial sound or a heart sound. The wrist, neck, and chest are disclosed as examples of the position of the body conduction sound sensor of the pulse measuring device.

CITATION LIST

Patent Literature

PTL 1: Japanese Patent Application Laid-open No. 2014-87387

SUMMARY OF INVENTION

Technical Problem

A pulse measuring method using sound such as the pulse measuring device disclosed in Patent Literature 1 is easily affected by noise. Therefore, deterioration of accuracy due to noise may be a problem, and further higher accuracy is required depending on the application.

The present invention intends to provide an information processing device, a wearable device, an information processing method, and a storage medium which can perform heartbeat measurement with high accuracy.

Solution to Problem

According to one example aspect of the present invention, provided is an information processing device including: an inspection signal generation unit configured to generate an inspection signal for emitting an inspection sound toward an ear canal of a subject; a first acoustic information acquisition unit configured to acquire a first acoustic information including information about an echo sound of the inspection sound; and a heartbeat information acquisition unit configured to acquire a heartbeat information about a heartbeat of the subject based on the first acoustic information.

According to another example aspect of the present invention, provided is a wearable device including: an inspection signal generation unit configured to generate an inspection signal for emitting an inspection sound toward an ear canal of a subject; a first acoustic information acquisition unit configured to acquire a first acoustic information including information about an echo sound of the inspection sound; and a heartbeat information acquisition unit configured to acquire a heartbeat information about a heartbeat of the subject based on the first acoustic information.

According to another example aspect of the present invention, provided is an information processing method including: generating an inspection signal for emitting an inspection sound toward an ear canal of a subject; acquiring a first acoustic information including information about an echo sound of the inspection sound; and acquiring a heartbeat information about a heartbeat of the subject based on the first acoustic information.

According to another example aspect of the present invention, provided is a storage medium storing a program that causes a computer to perform: generating an inspection signal for emitting an inspection sound toward an ear canal of a subject; acquiring a first acoustic information including information about an echo sound of the inspection sound; and acquiring a heartbeat information about a heartbeat of the subject based on the first acoustic information.

Advantageous Effects of Invention

According to the present invention, an information processing device, a wearable device, an information processing method, and a storage medium that can perform heartbeat measurement with high accuracy can be provided.

DESCRIPTION OF EMBODIMENTS

Exemplary example embodiments of the present invention will be described below with reference to the drawings. Throughout the drawings, the same components or corresponding components are labeled with same references, and the description thereof may be omitted or simplified.

First Example Embodiment

An information processing system according to the present example embodiment will be described. The information processing system of the present example embodiment is a system for acquiring a heartbeat signal about the heartbeat of a user (subject) wearing a wearable device such as an earphone.

Figure 1:
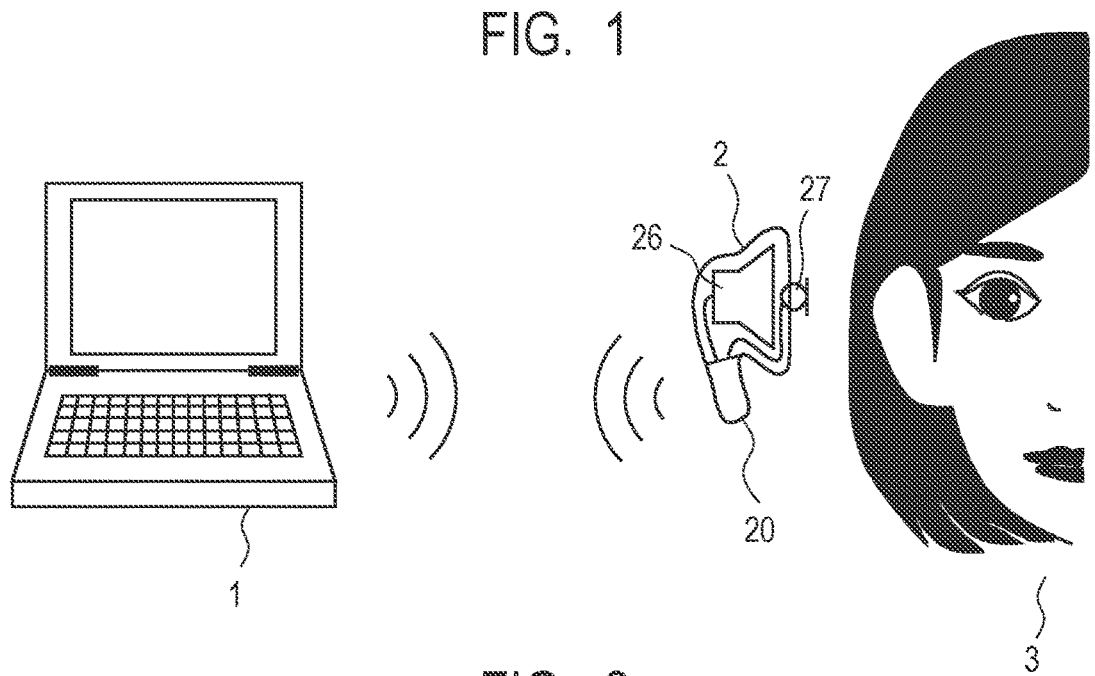
FIG. 1 is a schematic diagram illustrating a general configuration of an information processing system according to a first example embodiment.

FIG. 1 is a schematic diagram illustrating a general configuration of an information processing system according to the present example embodiment. The information processing system is provided with an information communication device 1 and an earphone 2 which may be connected to each other by wireless communication.

The earphone 2 includes an earphone control device 20, a speaker 26, and a microphone 27. The earphone 2 is an acoustic device which can be worn on the ear of the user 3, and is typically a wireless earphone, a wireless headset or the like. The speaker 26 functions as a sound wave generation unit which emits a sound wave toward the ear canal of the user 3 when worn, and is arranged on the wearing surface side of the earphone 2. The microphone 27 is also arranged on the wearing surface side of the earphone 2 so as to receive sound waves reflected by the ear canal or the like of the user 3 when the earphone is worn. The earphone control device 20 controls the speaker 26 and the microphone 27 and communicates with an information communication device 1.

Note that, in the present specification, "sound" such as sound waves and voices includes inaudible sounds whose frequency or sound pressure level is outside the audible range.

The information communication device 1 is, for example, a computer, and controls the operation of the earphone 2, transmits audio data for generating sound waves emitted from the earphone 2, and receives audio data acquired from the sound waves received by the earphone 2. As a specific example, when the user 3 listens to music using the earphone 2, the information communication device 1 transmits compressed data of music to the earphone 2. When the earphone 2 is a telephone device for business command at an event site, a hospital or the like, the information communication device 1 transmits audio data of the business instruction to the earphone 2. In this case, the audio data of the utterance of the user 3 may be transmitted from the earphone 2 to the information communication device 1. The information communication device 1 or the earphone 2 may have a function of otoacoustic authentication using sound waves received by the earphone 2. Further, the information communication device 1 or the earphone 2 may have a function of determining the wearing of the earphone 2 using sound waves received by the earphone 2.

Note that, the general configuration is an example, and for example, the information communication device 1 and the earphone 2 may be connected by wire. Further, the information communication device 1 and the earphone 2 may be configured as an integrated device, and further another device may be included in the information processing system.

Figure 2:
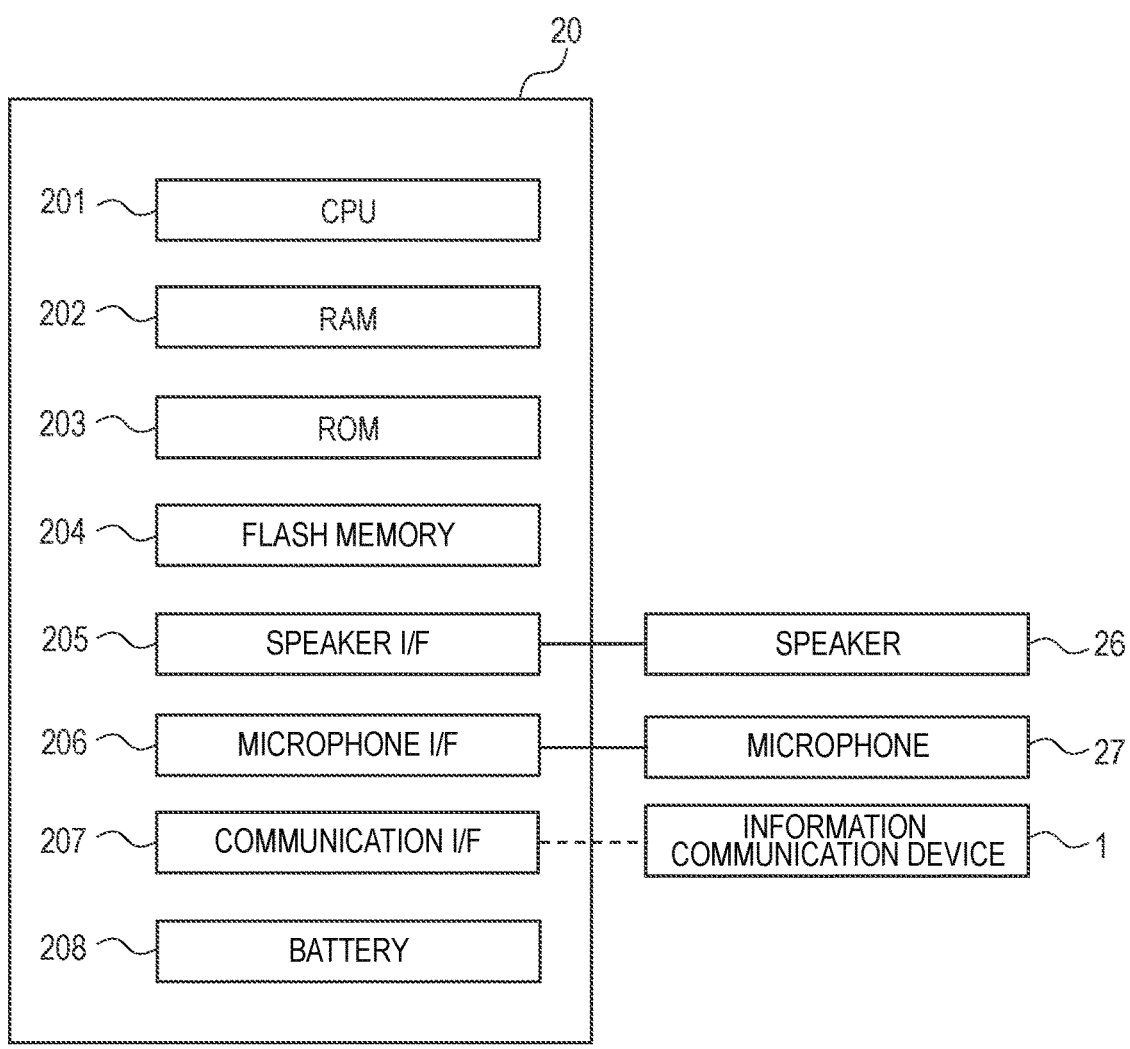
FIG. 2 is a block diagram illustrating a hardware configuration of an earphone according to the first example embodiment.

FIG. 2 is a block diagram illustrating a hardware configuration example of the earphone control device 20. The earphone control device 20 includes a central processing unit (CPU) 201, a random access memory (RAM) 202, a read only memory (ROM) 203, and a flash memory 204. The earphone control device 20 also includes a speaker interface (I/F) 205, a microphone I/F 206, a communication I/F 207, and a battery 208. Note that, each unit of the earphone control device 20 are connected to each other via a bus, wiring, a driving device, or the like (not illustrated).

The CPU 201 is a processor that has a function of performing a predetermined calculation according to a program stored in the ROM 203, the flash memory 204, or the like, and also controlling each unit of the earphone control device 20. The RAM 202 is composed of a volatile storage medium and provides a temporary memory area required for the operation of the CPU 201. The ROM 203 is composed of a non-volatile storage medium and stores necessary information such as a program used for the operation of the earphone control device 20. The flash memory 204 is a storage device composed of a non-volatile storage medium and temporarily storing data, storing an operation program of the earphone control device 20, or the like.

The communication I/F 207 is a communication interface based on standards such as Bluetooth (registered trademark) and Wi-Fi (registered trademark), and is a module for performing communication with the information communication device 1.

The speaker I/F 205 is an interface for driving the speaker 26. The speaker I/F 205 includes a digital-to-analog conversion circuit, an amplifier, or the like. The speaker I/F 205 converts the audio data into an analog signal and supplies the analog signal to the speaker 26. Thus, the speaker 26 emits sound waves based on the audio data.

The microphone I/F 206 is an interface for acquiring a signal from the microphone 27. The microphone I/F 206 includes an analog-to-digital conversion circuit, an amplifier, or the like. The microphone I/F 206 converts an analog signal generated by a sound wave received by the microphone 27 into a digital signal. Thus, the earphone control device 20 acquires audio data based on the received sound waves.

The battery 208 is, for example, a secondary battery, and supplies electric power required for the operation of the earphone 2. Thus, the earphone 2 can operate wirelessly without being connected to an external power source by wire.

Note that the hardware configuration illustrated in FIG. 2 is an example, and devices other than these may be added or some devices may not be provided. Further, some devices may be replaced with another device having similar functions. For example, the earphone 2 may further be provided with an input device such as a button so as to be able to receive an operation by the user 3, and further provided with a display device such as a display or a display lamp for providing information to the user 3. Thus, the hardware configuration illustrated in FIG. 2 can be appropriately changed.

Figure 3:
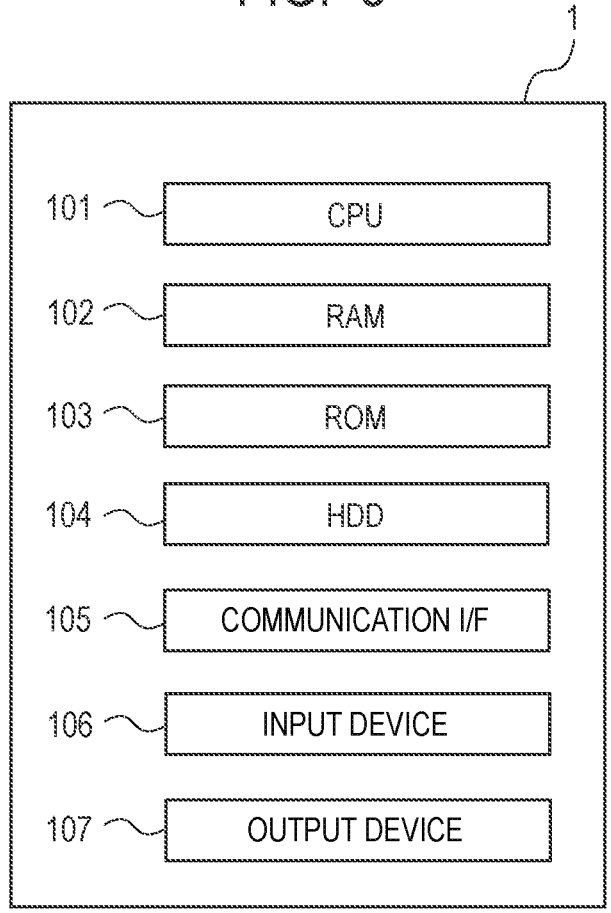
FIG. 3 is a block diagram illustrating a hardware configuration of an information communication device according to the first example embodiment.

FIG. 3 is a block diagram illustrating a hardware configuration example of the information communication device 1. The information communication device 1 includes a CPU 101, a RAM 102, a ROM 103, and a hard disk drive (HDD) 104. The information communication device 1 also includes a communication I/F 105, an input device 106, and an output device 107. Note that, each unit of the information communication device 1 is connected to each other via a bus, wiring, a driving device, or the like (not illustrated).

In FIG. 3, each unit constituting the information communication device 1 is illustrated as an integrated device, but some of these functions may be provided by an external device. For example, the input device 106 and the output device 107 may be external devices other than the unit constituting functions of a computer including the CPU 101 or the like.

The CPU 101 is a processor that has a function of performing a predetermined calculation according to a program stored in the ROM 103, the HDD 104, or the like, and also controlling each unit of the information communication device 1. The RAM 102 is composed of a volatile storage medium and provides a temporary memory area required for the operation of the CPU 101. The ROM 103 is composed of a non-volatile storage medium and stores necessary information such as a program used for the operation of the information communication device 1. The HDD 104 is a storage device composed of a non-volatile storage medium and temporarily storing data sent to and received from the earphone 2, storing an operation program of the information communication device 1, or the like.

The communication I/F 105 is a communication interface based on standards such as Bluetooth (registered trademark) and Wi-Fi (registered trademark), and is a module for performing communication with the other devices such as the earphone 2.

The input device 106 is a keyboard, a pointing device, or the like, and is used by the user 3 to operate the information communication device 1. Examples of the pointing device include a mouse, a trackball, a touch panel, and a pen tablet.

The output device 107 is, for example, a display device. The display device is a liquid crystal display, an organic light emitting diode (OLED) display, or the like, and is used for displaying information, graphical user interface (GUI) for operation input, or the like. The input device 106 and the output device 107 may be integrally formed as a touch panel.

Note that, the hardware configuration illustrated in FIG. 3 is an example, and devices other than these may be added or some devices may not be provided. Further, some devices may be replaced with other devices having similar functions. Further, some of the functions of the present example embodiment may be provided by another device via a network, or the functions of the present example embodiment may be realized by being distributed to a plurality of devices. For example, the HDD 104 may be replaced with a solid state drive (SSD) using a semiconductor memory, or may be replaced with a cloud storage. Thus, the hardware configuration illustrated in FIG. 3 can be appropriately changed.

Figure 4:
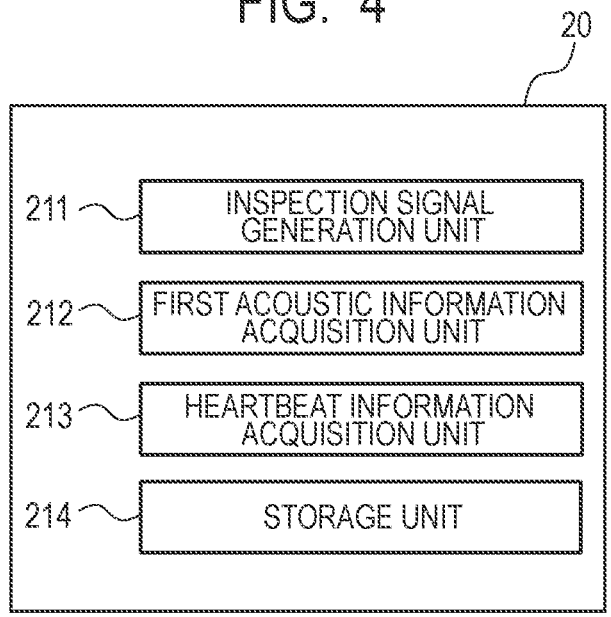
FIG. 4 is a functional block diagram of an earphone control device according to the first example embodiment.

FIG. 4 is a functional block diagram of the earphone control device 20 according to the present example embodiment. The earphone control device 20 includes an inspection signal generation unit 211, a first acoustic information acquisition unit 212, a heartbeat information acquisition unit 213 and a storage unit 214.

The CPU 201 loads programs stored in the ROM 203, the flash memory 204, or the like into the RAM 202 and executes them. Thus, the CPU 201 realizes the functions of the inspection signal generation unit 211, the first acoustic information acquisition unit 212, and the heartbeat information acquisition unit 213. Further, the CPU 201 controls the flash memory 204 based on the program to realize the function of the storage unit 214. The specific process performed in each of these units will be described later.

Note that, some or all of the functions of the functional blocks of FIG. 4 may be provided in the information communication device 1 instead of the earphone control device 20. That is, each function described above may be realized by the earphone control device 20, may be realized by the information communication device 1, or may be realized by cooperation between the information communication device 1 and the earphone control device 20. The information communication device 1 and the earphone control device 20 are sometimes generally referred to as information processing devices.

However, it is desirable that the heartbeat information acquisition process of the present example embodiment is performed by the earphone control device 20 provided in the earphone 2. In this case, the communication between the information communication device 1 and the earphone 2 in the heartbeat information acquisition process can be made unnecessary, and the power consumption of the earphone 2 can be reduced. Since the earphone 2 is a wearable device, it is required to be small in size. Therefore, the size of the battery 208 is limited, and it is difficult to use a battery having a large discharge capacity. Under such circumstances, it is effective to reduce power consumption by completing the heartbeat information acquisition process in the earphone 2. In the following description, each function of the function block of FIG. 4 is assumed to be provided in the earphone 2 unless otherwise noted.

Figure 5:
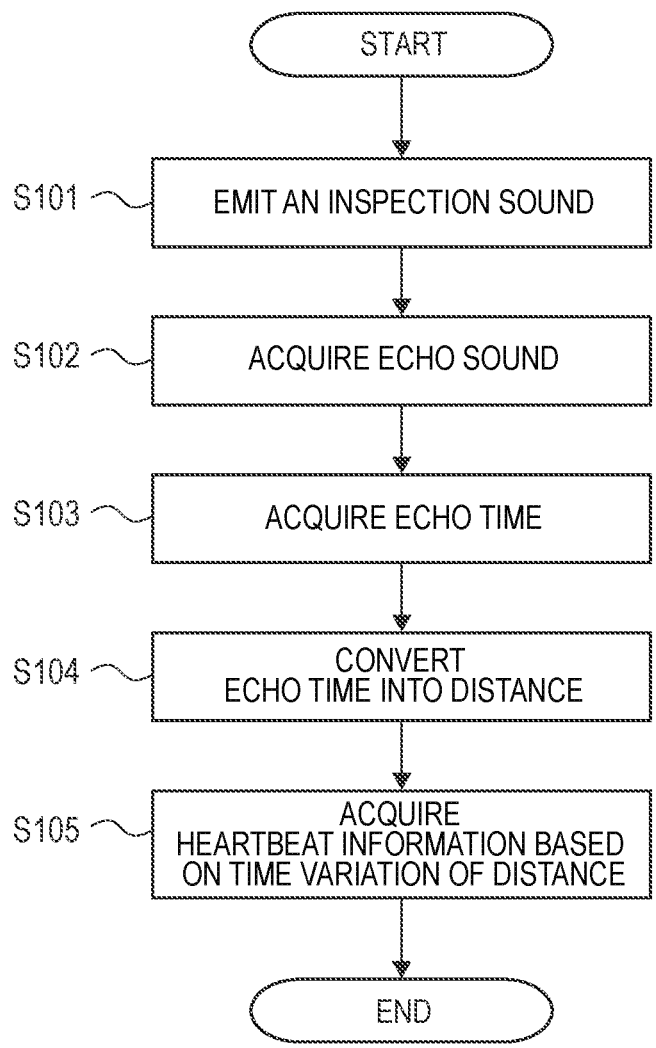
FIG. 5 is a flowchart illustrating a heartbeat information acquisition process performed by the earphone control device according to the first example embodiment.

FIG. 5 is a flowchart illustrating heartbeat information acquisition process performed by the earphone control device 20 according to the present example embodiment. The operation of the earphone control device 20 will be described with reference to FIG. 5.

The heartbeat information acquisition process in FIG. 5 is performed, for example, every time a predetermined time elapses when the power of the earphone 2 is on. Alternatively, the heartbeat information acquisition process in FIG. 5 may be performed when the user 3 starts using the earphone 2 by operating the earphone 2. The execution timing of the heartbeat information acquisition process in FIG. 5 may be based on an instruction from the information communication device 1.

In step S101, the inspection signal generation unit 211 generates an inspection signal. The earphone control device 20 transmits an inspection signal via the speaker I/F 205 to the speaker 26. Thus, the speaker 26 emits an inspection sound for acquiring heartbeat information toward the ear canal of the user 3. The inspection sound is reflected by an eardrum located behind the ear canal of the user 3, and the echo sound is received by the microphone 27. Note that, it is desirable that the inspection sound be an ultrasonic wave, and thereby the discomfort caused by the inspection sound is reduced. As the specific frequency of the ultrasonic wave, for example, 40 kHz which is sufficiently higher than the audible range may be selected.

In step S102, the first acoustic information acquisition unit 212 acquires acoustic information based on the echo sound received by the microphone 27. This acoustic information is stored in the storage unit 214 as first acoustic information including information about the echo sound of the inspection sound. The first acoustic information acquisition unit 212 may appropriately perform signal process such as Fourier transform, correlation calculation, noise removal, and level correction in acquiring the first acoustic information.

In steps S103 to S105, the heartbeat information acquisition unit 213 acquires heartbeat information about a heartbeat of the user 3 based on the first acoustic information. Although this process will be described with reference to FIG. 5, each of the processes in steps S103 to S105 is an example, and the heartbeat information may be acquired by another method, or a part of the process may be omitted.

In step S103, the heartbeat information acquisition unit 213 refers to the inspection signal and the first acoustic information to acquire the echo time that is the time difference between the inspection sound emitted from the speaker 26 and the echo sound received by the microphone 27. The echo time is stored in the storage unit 214.

In step S104, the heartbeat information acquisition unit 213 converts the echo time into a distance. This conversion is calculated by L=VT (Equation 1) where L is the distance, T is the echo time, and V is the speed of sound in air. For example, if the echo time T is 160 μs and the speed of sound V in the air is 340 m/s, the distance L is calculated as 54.4 mm by substituting these values into Equation 1. The distance L corresponds to twice the distance from the earphone 2 to the eardrum, that is, twice the length of the ear canal.

In step S105, the heartbeat information acquisition unit 213 acquires the heartbeat information based on the time variation of the distance L. The eardrum also oscillates in synchronization with changes in blood flow when blood flow is cyclically altered by the heartbeat. Therefore, the distance L between the earphone 2 and the eardrum acquired by the heartbeat information acquisition unit 213 also changes in a cycle synchronized with the heartbeat. Therefore, the heartbeat information acquisition unit 213 can acquire the heartbeat information about the heartbeat from the time variation of the distance L. The heartbeat information may be, for example, a waveform of the heartbeat, a heartbeat within a predetermined time period, or an interval between peaks of the heartbeat.

A specific example of the inspection signal generated by the inspection signal generation unit 211 will be described. Examples of signals used to generate the inspection sound waves may be modulated signals that include a modulation portion in which at least one of amplitude, frequency, and phase is modulated, or chirp signals in which the frequency varies with time.

Figure 6:
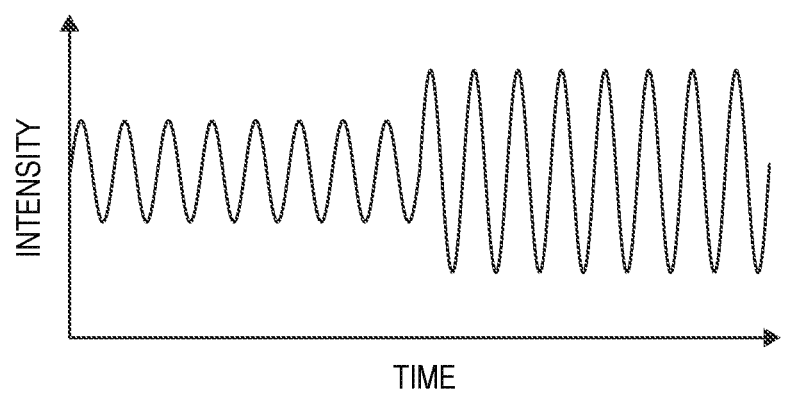
FIG. 6 is a graph illustrating an example of an inspection signal.

FIG. 6 is a graph illustrating an example of an inspection signal by pulse amplitude modulation (PAM). In FIG. 6, the vertical axis indicates intensity, and the horizontal axis indicates time. As illustrated in FIG. 6, the inspection signal has a waveform having a modulation portion whose amplitude is modulated.

Figure 7:
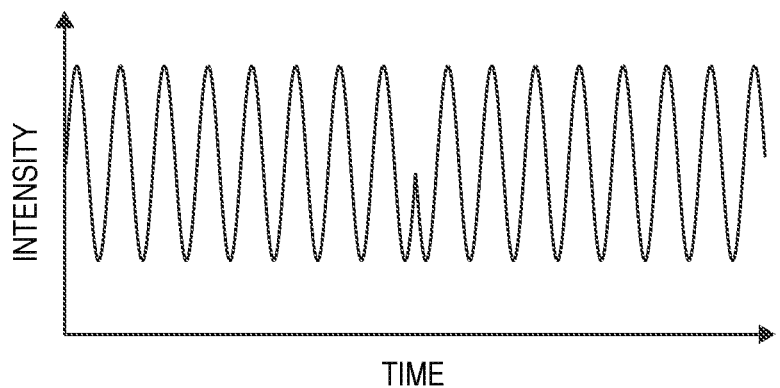
FIG. 7 is a graph illustrating an example of an inspection signal.

FIG. 7 is a graph illustrating an example of an inspection signal by pulse phase modulation (PPM). As illustrated in FIG. 7, the inspection signal has a waveform having a modulation portion whose phase is modulated.

Figure 8:
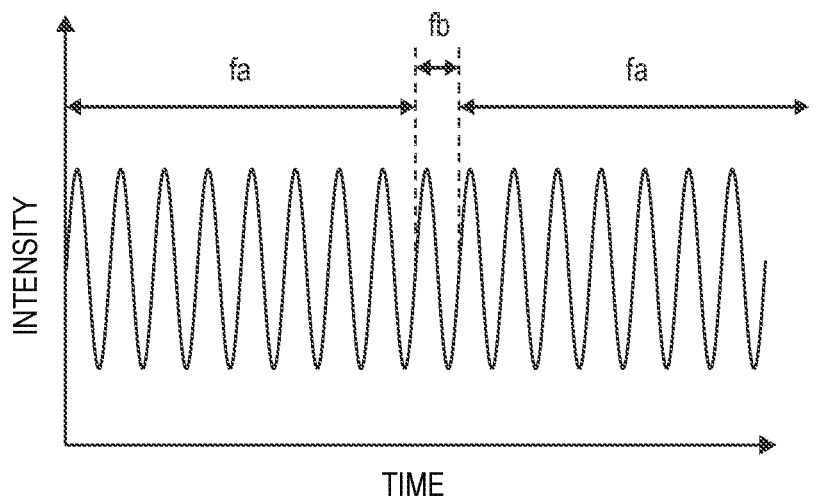
FIG. 8 is a graph illustrating an example of an inspection signal.

FIG. 8 is a graph illustrating an example of an inspection signal by pulse frequency modulation (PFM). In FIG. 8, fa and fb denote different frequencies. In other words, as illustrated in FIG. 8, the inspection signal has a waveform having a modulation portion whose frequency is modulated.

Figure 9:
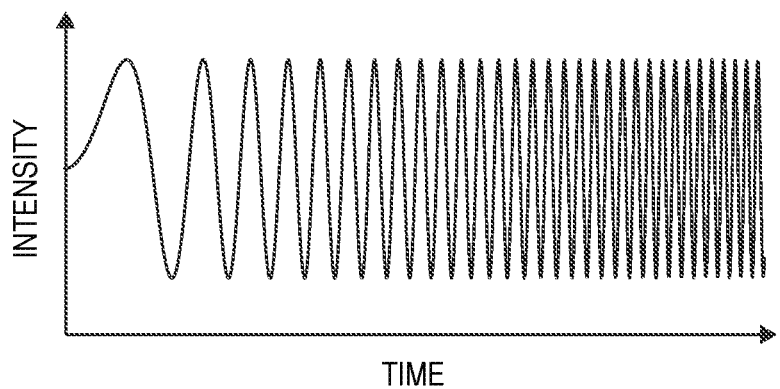
FIG. 9 is a graph illustrating an example of an inspection signal.

FIG. 9 is a graph illustrating an example where the inspection signal is a chirp signal. As illustrated in FIG. 9, the inspection signal has a chirp wave waveform whose frequency varies with time.

Figure 10:
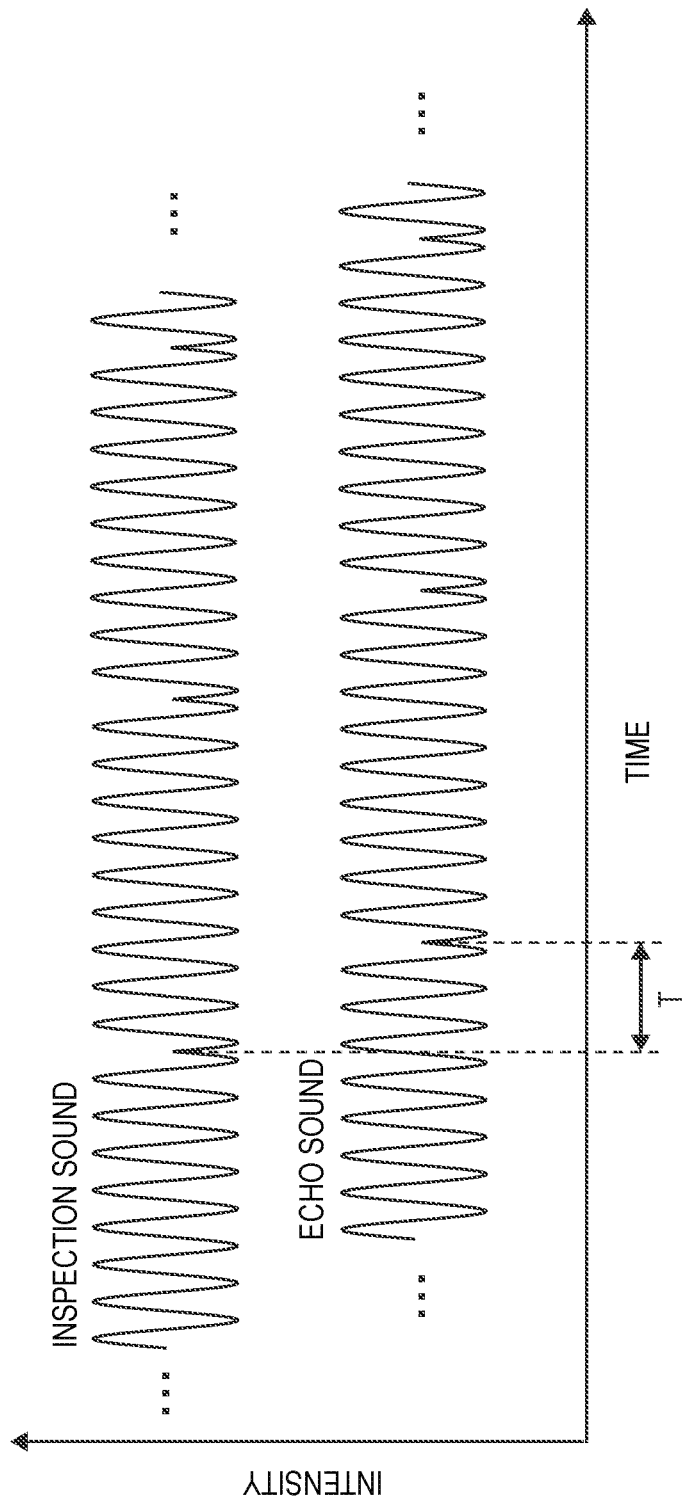
FIG. 10 is a graph illustrating a relation between an inspection sound and an echo sound.

A method for acquiring the echo time T will be described with a specific example. FIG. 10 is a graph illustrating an example of the characteristics of the echo sound when the inspection sound is a pulse phase modulated wave. The waveform of the inspection sound is illustrated in the upper part of FIG. 10, and the waveform of the echo sound is illustrated in the lower part of FIG. 10. As illustrated in FIG. 10, the modulation portion of the inspection sound and the modulation portion of the echo sound are shifted in the time axis direction by the echo time T. Therefore, in the process of step S103, the heartbeat information acquisition unit 213 can acquire the echo time T by detecting the time difference with the modulation portion of the inspection sound and the modulation portion of the echo sound as a reference. Note that, the same applies to the case where pulse amplitude modulation or pulse phase modulation is used.

Figure 11:
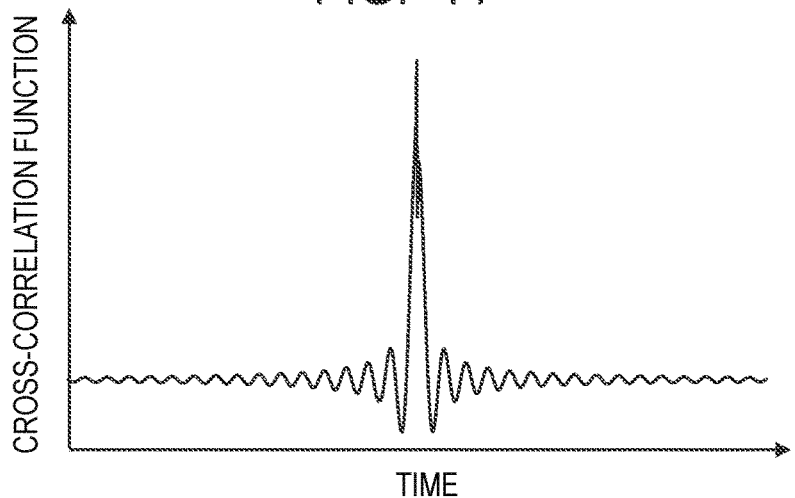
FIG. 11 is a graph illustrating an example of a cross-correlation function of the inspection sound and the echo sound in the case the inspection sound has a chirp wave.

Another example of a method for acquiring the echo time T will be described. FIG. 11 is a graph illustrating an example of a cross-correlation function between an inspection sound and an echo sound when the inspection sound has a chirp wave. When the inspection sound has a chirp wave, a technique called pulse compression can be applied to enhance the peak by calculating the cross-correlation function between the inspection sound and the echo sound. In the present method, as illustrated in FIG. 11, a pulse with a large amplitude appears at a position corresponding to a time difference between the inspection sound and the echo sound. Accordingly, the echo time T can be acquired, and the S/N ratio (Signal-to-Noise Ratio) of the signal can be improved. Thus, in an example in which the chirp wave is used as the inspection sound and the echo time is acquired by using the result of the correlation operation between the inspection sound and the echo sound, the noise can be more effectively eliminated.

According to the present example embodiment, the inspection sound is emitted toward the ear canal of the user 3, and the heartbeat information of the subject can be acquired based on the echo sound of the inspection sound. Thus, since the pulse in the ear canal of the user 3 can be directly acquired, the influence of noise can be reduced. Accordingly, it is possible to provide an information processing device capable of performing heartbeat measurement with high accuracy.

The heartbeat information may be used for health management of the user 3, for example. By implementing a function for acquiring heartbeat information on the earphone 2, the user 3 can monitor the heartbeat and record exercise intensity by wearing the earphone 2 during exercise, for example. Also, the user 3 can detect the sign of the disease early by monitoring the fluctuation of the heartbeat by wearing the earphone 2 at rest.

Second Example Embodiment

The information processing system of the present example embodiment is different from the first example embodiment in that the earphone 2 further acquires second acoustic information to acquire heartbeat information. In the following, differences from the first example embodiment will be mainly described, and description of common parts will be omitted or simplified.

Figure 12:
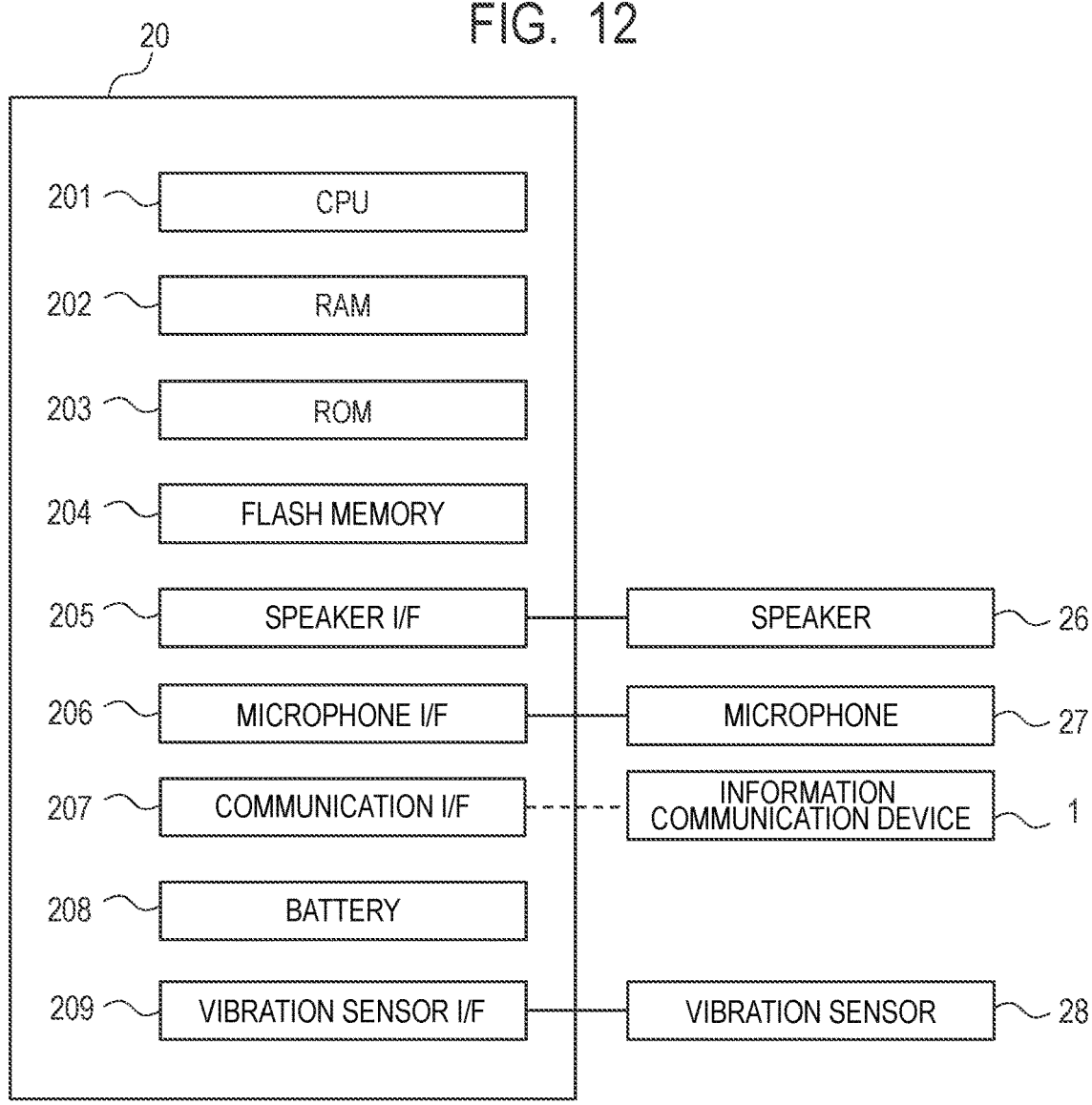
FIG. 12 is a block diagram illustrating a hardware configuration of an earphone according to a second example embodiment.

FIG. 12 is a block diagram illustrating a hardware configuration example of the earphone 2 and the earphone control device 20 according to the present example embodiment. In the present example embodiment, the earphone 2 further includes a vibration sensor 28. The vibration sensor 28 is arranged to detect the vibration derived from the pulse of the blood vessel near the ear of the user 3.

Further, the earphone control device 20 includes a vibration sensor I/F 209. The vibration sensor I/F 209 is an interface for acquiring a signal from the vibration sensor 28. The vibration sensor I/F 209 includes an analog-to-digital conversion circuit, an amplifier, or the like. The microphone I/F 206 converts the analog signal generated by the vibration received by the vibration sensor 28 into a digital signal. Thus, the earphone control device 20 acquires vibration data based on the received vibration.

Figure 13:
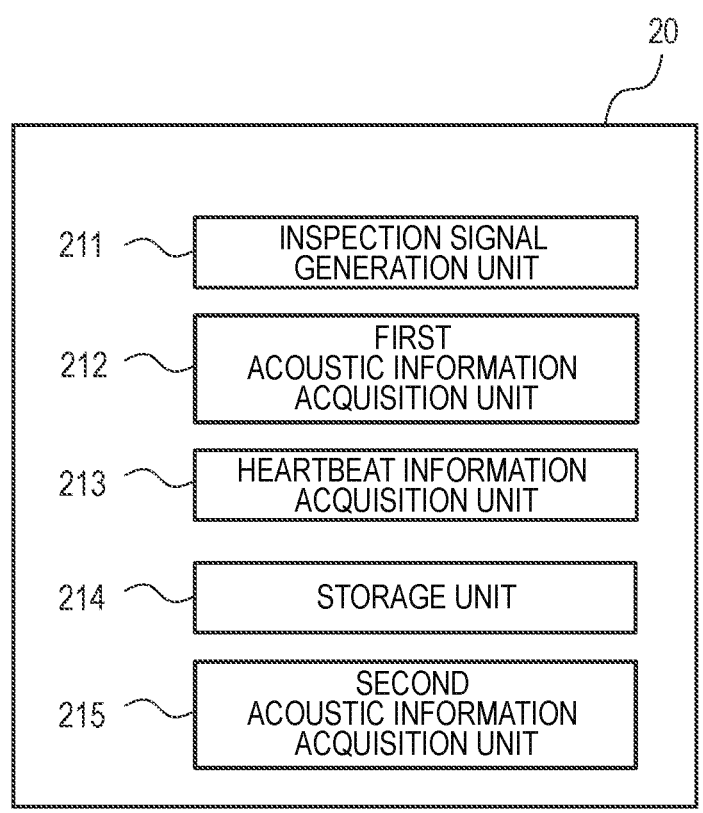
FIG. 13 is a functional block diagram of an earphone control device according to the second example embodiment.

FIG. 13 is a functional block diagram of the earphone control device 20 according to the present example embodiment. The earphone control device 20 further includes a second acoustic information acquisition unit 215. The CPU 201 loads the programs stored in the ROM 203, the flash memory 204, or the like into the RAM 202 and executes them, thereby realizing the functions of the second acoustic information acquisition unit 215. This function may be provided in the information communication device 1.

Figure 14:
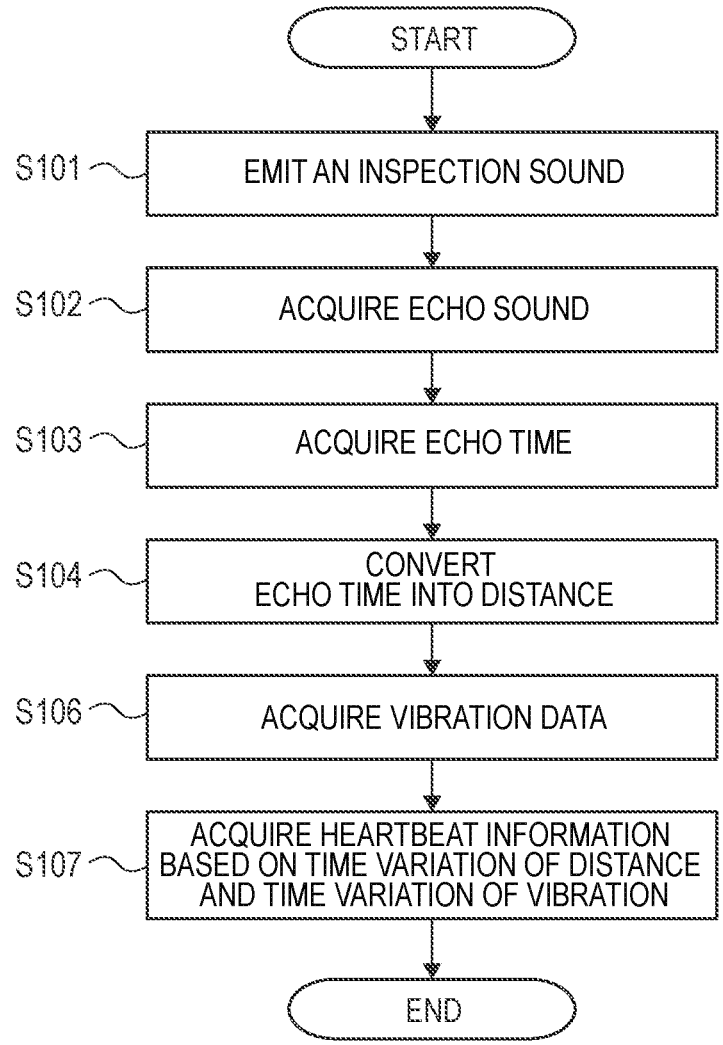
FIG. 14 is a flowchart illustrating a heartbeat information acquisition process performed by the earphone control device according to the second example embodiment.

FIG. 14 is a flowchart illustrating heartbeat information acquisition process performed by the earphone control device 20 according to the present example embodiment. Referring to FIG. 14, the operation of the earphone control device 20 will be described. In the heartbeat information acquisition process of the present example embodiment, the processes from step S101 to step S104 are the same as those of the first example embodiment, and the description thereof is omitted.

In step S106, the second acoustic information acquisition unit 215 acquires acoustic information based on the vibration received by the vibration sensor 28. The acoustic information is stored in the storage unit 214 as second acoustic information different from the first acoustic information. Note that, the second acoustic information acquisition unit 215 may appropriately perform signal process such as Fourier transform, correlation calculation, noise removal, and level correction in acquiring the second acoustic information. Note that, the process in step S106 may be performed before the processes in steps S101 to S104, or may be performed in parallel with the processes in steps S101 to S104.

Here, the first acoustic information includes information of a signal of frequency of an inspection sound which is an ultrasonic wave, while the second acoustic information includes information of a signal of a frequency of vibration derived from a heartbeat. That is, the second acoustic information includes information of a signal having a frequency lower than the frequency of the inspection sound. Thus, two kinds of signals acquired based on sounds of different frequencies can be acquired.

In step S107, the heartbeat information acquisition unit 213 acquires heartbeat information based on the time variation of the distance L as the first acoustic information and the time variation of the vibration data as the second acoustic information. In this acquisition, the heartbeat information acquisition unit 213 calculates a cross-correlation function between the time variation of the first acoustic information and the distance L and the time variation of the vibration data to extract information of the time variation of the heartbeat included in both signals.

By using the two kinds of signals, the influence of noise generated inside the body or the like of the user 3 and noise from the outside is canceled, and the frequency component of the heartbeat commonly included in both signals is enhanced. Accordingly, it is possible to provide an information processing device capable of performing heartbeat measurement with higher accuracy.

Note that, in the present example embodiment, the means for acquiring the second acoustic information is not limited to the vibration sensor 28, but may be, for example, a light detection type pulse sensor which irradiates the body surface with a laser beam to observe the amount of blood flow flowing through the blood vessel. The means for acquiring the second acoustic information is not limited to those incorporated in the earphone 2, and the vibration sensor 28 may be provided on a wrist band of a smart watch or the like so as to detect a pulse from a blood vessel of an arm such as a radial artery, for example.

The system described in the above example embodiment can be configured as in the following third example embodiment.

Third Example Embodiment

Figure 15:
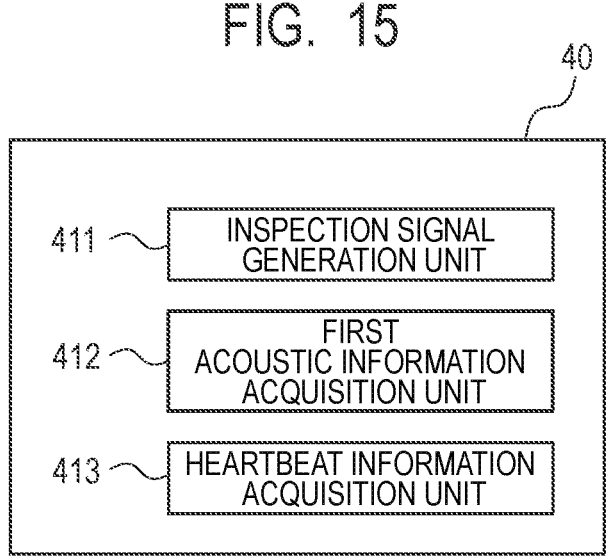
FIG. 15 is a functional block diagram of an information processing device according to a third example embodiment.

FIG. 15 is a functional block diagram of the information processing device 40 according to the third example embodiment. The information processing device 40 includes an inspection signal generation unit 411, a first acoustic information acquisition unit 412, and a heartbeat information acquisition unit 413. The inspection signal generation unit 411 generates an inspection signal for emitting an inspection sound toward the ear canal of the subject. The first acoustic information acquisition unit 412 acquires first sound information including information about the echo sound of the inspection sound. The heartbeat information acquisition unit 413 acquires heartbeat information about the heartbeat of the subject based on the first sound information.

According to the present example embodiment, there is provided an information processing device 40 capable of performing heartbeat measurement with high accuracy.

MODIFIED EXAMPLE EMBODIMENTS

The present invention is not limited to the example embodiments described above, and may be suitably modified within the scope of the present invention. For example, an example in which a part of the configuration of one embodiment is added to another embodiment or an example in which a part of the configuration of another embodiment is replaced is also an example embodiment of the present invention.

The scope of each of the example embodiments also includes a processing method that stores, in a storage medium, a program that causes the configuration of each of the example embodiments to operate so as to implement the function of each of the example embodiments described above, reads the program stored in the storage medium as a code, and executes the program in a computer. That is, the scope of each of the example embodiments also includes a computer readable storage medium. Further, each of the example embodiments includes not only the storage medium in which the computer program described above is stored but also the computer program itself. Further, one or two or more components included in the example embodiments described above may be a circuit such as an application specific integrated circuit (ASIC), a field programmable gate array (FPGA), or the like configured to implement the function of each component.

As the storage medium, for example, a floppy (registered trademark) disk, a hard disk, an optical disk, a magneto-optical disk, a compact disk (CD)-ROM, a magnetic tape, a nonvolatile memory card, or a ROM can be used. Further, the scope of each of the example embodiments includes an example that operates on operating system (OS) to perform a process in cooperation with another software or a function of an add-in board without being limited to an example that performs a process by an individual program stored in the storage medium.

Further, a service implemented by the function of each of the example embodiments described above may be provided to a user in a form of software as a service (SaaS).

It should be noted that the above-described embodiments are merely examples of embodying the present invention, and the technical scope of the present invention should not be limitedly interpreted by these. That is, the present invention can be implemented in various forms without departing from the technical idea or the main features thereof.

The whole or part of the example embodiments disclosed above can be described as, but not limited to, the following supplementary notes.

(Supplementary Note 1)

An information processing device comprising: an inspection signal generation unit configured to generate an inspection signal for emitting an inspection sound toward an ear canal of a subject;
a first acoustic information acquisition unit configured to acquire a first acoustic information including information about an echo sound of the inspection sound; and a heartbeat information acquisition unit configured to acquire a heartbeat information about a heartbeat of the subject based on the first acoustic information.

(Supplementary Note 2)

The information processing device according to supplementary note 1, wherein the first acoustic information includes an information about a vibration of an eardrum of the subject.

(Supplementary Note 3)

The information processing device according to supplementary note 1 or 2, wherein the heartbeat information acquisition unit acquires the heartbeat information based on an echo time between emitting the inspection sound and acquiring the echo sound.

(Supplementary Note 4)

The information processing device according to supplementary note 3, wherein the heartbeat information acquisition unit acquires the heartbeat information based on the echo time or a time variation of a distance calculated from the echo time.

(Supplementary Note 5)

The information processing device according to supplementary note 3 or 4, wherein a waveform of the inspection sound includes a modulation portion in which at least one of amplitude, frequency and phase is modulated, and wherein the heartbeat information acquisition unit acquires the echo time based on a time difference of a modulation portion included in the inspection sound and the echo sound.

(Supplementary Note 6)

The information processing device according to supplementary note 3 or 4, wherein the inspection sound has a chirp wave in which frequency varies with time, and wherein the heartbeat information acquisition unit acquires the echo time based on a result of a correlation calculation of the inspection sound and the echo sound.

(Supplementary Note 7)

The information processing device according to any one of supplementary notes 1 to 6, wherein the inspection sound is an ultrasonic wave having higher frequency than an audible range.

(Supplementary Note 8)

The information processing device according to any one of supplementary notes 1 to 7 further comprising a second acoustic information acquisition unit configured to acquire a second acoustic information including information of a signal having lower frequency than frequency of the inspection sound, wherein the heartbeat information acquisition unit acquires the heartbeat information based on the first acoustic information and the second acoustic information.

(Supplementary Note 9)

The information processing device according to supplementary note 8, wherein the second acoustic information includes information about a vibration of a position other than the ear canal of the subject.

(Supplementary Note 10)

The information processing device according to supplementary note 8 or 9, wherein the heartbeat information acquisition unit acquires the heartbeat information based on a result of a correlation calculation of the first acoustic information and the second acoustic information.

(Supplementary Note 11)

A wearable device comprising: an inspection signal generation unit configured to generate an inspection signal for emitting an inspection sound toward an ear canal of a subject;
a first acoustic information acquisition unit configured to acquire a first acoustic information including information about an echo sound of the inspection sound; and
a heartbeat information acquisition unit configured to acquire a heartbeat information about a heartbeat of the subject based on the first acoustic information.

(Supplementary Note 12)

An information processing method comprising: generating an inspection signal for emitting an inspection sound toward an ear canal of a subject;
acquiring a first acoustic information including information about an echo sound of the inspection sound; and
acquiring a heartbeat information about a heartbeat of the subject based on the first acoustic information.

(Supplementary Note 13)

A storage medium storing a program that causes a computer to perform:
generating an inspection signal for emitting an inspection sound toward an ear canal of a subject;
acquiring a first acoustic information including information about an echo sound of the inspection sound; and
acquiring a heartbeat information about a heartbeat of the subject based on the first acoustic information.

REFERENCE SIGNS LIST 1 information communication device
2 earphone
3 user
20 earphone control device
26 speaker
27 microphone
40 information processing device
101, 201 CPU
102, 202 RAM
103, 203 ROM
104 HDD
105, 207 communication I/F
106 input device
107 output device
204 flash memory
205 speaker I/F
206 microphone I/F
208 battery
211, 411 inspection signal generation unit
212, 412 first acoustic information acquisition unit
213, 413 heartbeat information acquisition unit
214 storage unit
215 second acoustic information acquisition unit

What is claimed is:
1. An information processing device comprising:
a memory configured to store instructions; and
a processor configured to execute the instructions to:
generate an inspection signal for emitting an inspection sound toward an ear canal of a subject, wherein the inspection sound is an ultrasonic wave having higher frequency than an audible range;

acquire a first acoustic information including information about an echo sound of the inspection sound, wherein the first acoustic information includes an information about a vibration of an eardrum of the subject; and acquire a heartbeat information about a heartbeat of the subject based on the first acoustic information.

2. The information processing device according to claim 1, wherein the heartbeat information is acquired based on an echo time between emitting the inspection sound and acquiring the echo sound.

3. The information processing device according to claim 2, wherein the heartbeat information is acquired based on the echo time or a time variation of a distance calculated from the echo time.

4. The information processing device according to claim 2, wherein a waveform of the inspection sound includes a modulation portion in which at least one of amplitude, frequency and phase is modulated, and wherein the echo time is acquired based on a time difference of the modulation portion included in the inspection sound and the echo sound.

5. The information processing device according to claim 2, wherein the inspection sound has a chirp wave in which frequency varies with time, and wherein the echo time is acquired based on a result of a correlation calculation of the inspection sound and the echo sound.

6. The information processing device according to claim 1, wherein the processor is further configured to execute the instructions to acquire a second acoustic information including information of a signal having lower frequency than frequency of the inspection sound, wherein the heartbeat information is acquired based on the first acoustic information and the second acoustic information.

7. The information processing device according to claim 6, wherein the second acoustic information includes information about a vibration of a position other than the ear canal of the subject.

8. The information processing device according to claim 6, wherein the heartbeat information is acquired based on a result of a correlation calculation of the first acoustic information and the second acoustic information.

9. An information processing method comprising:

generating an inspection signal for emitting an inspection sound toward an ear canal of a subject, wherein the inspection sound is an ultrasonic wave having higher frequency than an audible range;

acquiring a first acoustic information including information about an echo sound of the inspection sound, wherein the first acoustic information includes an information about a vibration of an eardrum of the subject; and acquiring a heartbeat information about a heartbeat of the subject based on the first acoustic information.

10. A non-transitory storage medium storing a program that causes a computer to perform:

generating an inspection signal for emitting an inspection sound toward an ear canal of a subject, wherein the inspection sound is an ultrasonic wave having higher frequency than an audible range;

acquiring a first acoustic information including information about an echo sound of the inspection sound, wherein the first acoustic information includes an information about a vibration of an eardrum of the subject; and acquiring a heartbeat information about a heartbeat of the subject based on the first acoustic information.

* * * * *